United States Patent
Imura

(10) Patent No.: US 8,115,924 B2
(45) Date of Patent: Feb. 14, 2012

(54) OPTICAL CHARACTERISTIC MEASURING APPARATUS

(75) Inventor: Kenji Imura, Toyohashi (JP)

(73) Assignee: Konica Minolta Sensing, Inc., Osaka (JP)

(\*) Notice: Subject to any disclaimer, the term of this patent is extended or adjusted under 35 U.S.C. 154(b) by 296 days.

(21) Appl. No.: 12/589,410

(22) Filed: Oct. 22, 2009

(65) Prior Publication Data

US 2010/0103407 A1 Apr. 29, 2010

(30) Foreign Application Priority Data

Oct. 29, 2008 (JP) ................................. 2008-278795

(51) Int. Cl.
*G01J 3/00* (2006.01)
(52) U.S. Cl. ........................... 356/328; 356/73; 356/402
(58) Field of Classification Search ................. 356/72, 356/73, 326, 328, 402
See application file for complete search history.

(56) References Cited

U.S. PATENT DOCUMENTS 7,502,099 B2    3/2009  Imura

FOREIGN PATENT DOCUMENTS

JP    2006-292510    10/2006

*Primary Examiner* — F. L. Evans
(74) *Attorney, Agent, or Firm* — Brinks Hofer Gilson & Lione

(57) ABSTRACT

An optical characteristic measuring apparatus of the invention includes a sequentially-readable charge storage sensor array having a plurality of light receiving elements. Irradiation of first illumination light and second illumination light is controlled in such a manner that a period for irradiating the second illumination light onto a sample containing a fluorescent material is included in an integration period of each of the light receiving elements for receiving a wavelength component of fluoresced light from the sample in measuring an optical characteristic of the sample. The optical characteristic measuring apparatus having the above arrangement enables to accurately measure the optical characteristics of samples containing a fluorescent material in a short time by scanning the samples.

7 Claims, 8 Drawing Sheets

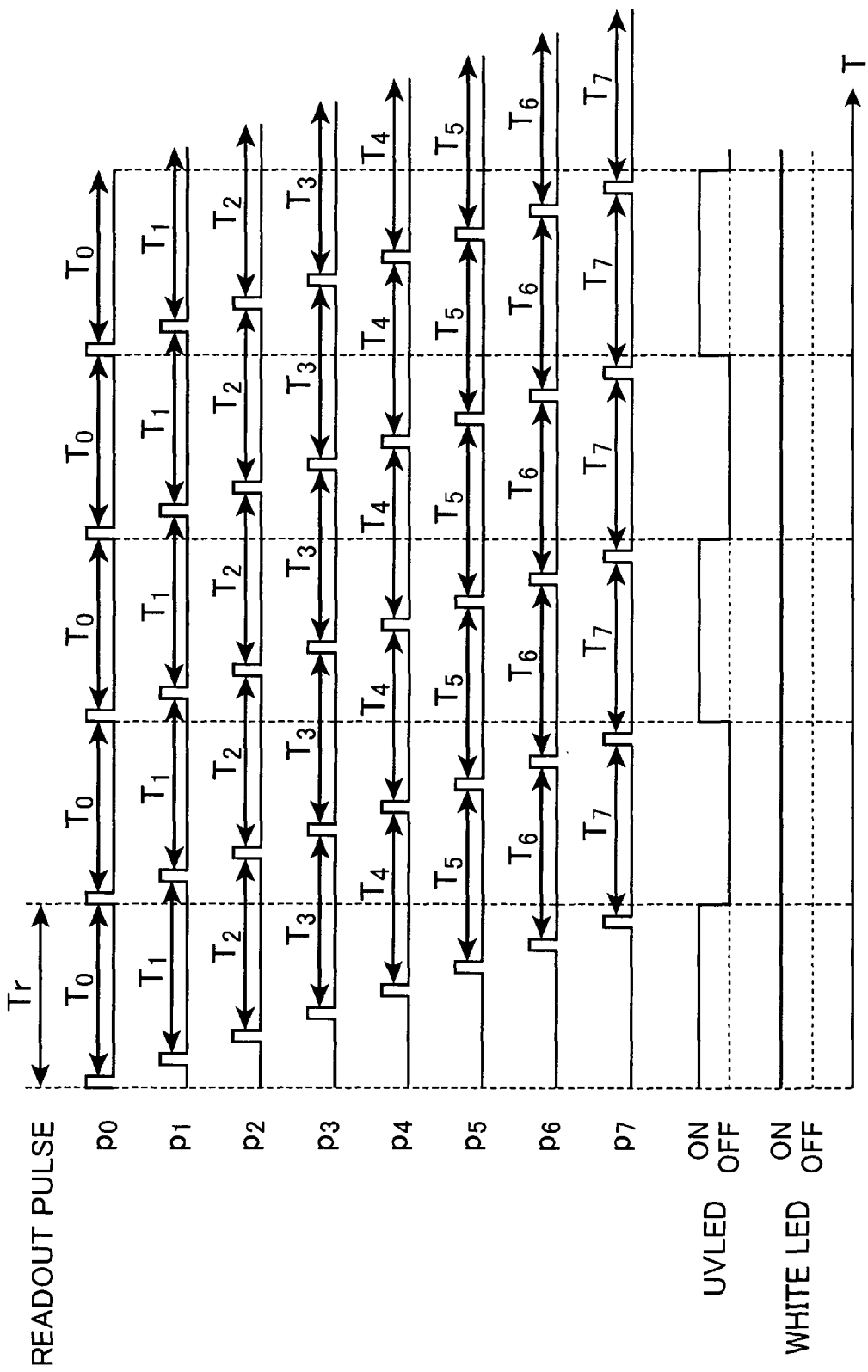

OPTICAL CHARACTERISTIC MEASURING APPARATUS

This application is based on Japanese Patent Application No. 2008-278795 filed on Oct. 29, 2008, the contents of which are hereby incorporated by reference.

BACKGROUND OF THE INVENTION AND RELATED ART STATEMENT

1. Field of the Invention

The present invention relates to an optical characteristic measuring apparatus for measuring a spectral characteristic of a sample exhibiting fluorescence.

2. Description of the Related Art

In recent years, many of white paper and fabrics are treated by a fluorescent whitening agent (FWA). It is impossible or difficult to precisely evaluate the whiteness (degree of whiteness or brightness) or the hue of these products, without considering an influence of fluoresced light. In view of the above, there is a demand for improvement in colorimetry of FWA-treated paper or fabrics, considering an influence of fluoresced light.

Generally, a visible optical characteristic of a reflecting sample is expressed by a relative ratio to the perfect white. Specifically, a visible optical characteristic of a reflecting sample is expressed by the total spectral radiance factor $B(\lambda)$. The total spectral radiance factor $B(\lambda)$ is the ratio of light emitted from a reflecting sample in a certain illuminating condition and a certain receiving condition, to light emitted from a perfect reflecting diffuser in the identical illuminating and receiving conditions at each wavelength $\lambda$.

In an FWA-treated sample i.e. a sample containing a fluorescent material (hereinafter, called as a fluorescent sample), a color of fluoresced light is observed as an objective color, wherein reflected light is superimposed on the fluoresced light. In other words, light emitted from a fluorescent sample is given as the sum of reflected light (reflected light component) and fluoresced light (fluorescent light component) from a fluorescent sample. Accordingly, similarly to the above, the total spectral radiance factor $B(\lambda)$ of a fluorescent sample is given as the sum of the reflection spectral radiance factor $R(\lambda)$ and the fluorescent spectral radiance factor $F(\lambda)$, which are the ratios of light reflected and fluoresced from the fluorescent sample in a certain illuminating condition and a certain receiving condition respectively, to light from a perfect reflecting diffuser in the identical illuminating and receiving conditions.

The above-mentioned perfect reflecting diffuser has no fluorescence, and the reflectivity thereof has no dependence on the wavelength of illumination light. Accordingly, the above-mentioned total spectral radiance factor $B(\lambda)$, reflection spectral radiance factor $R(\lambda)$ and fluorescent spectral radiance factor $F(\lambda)$ are expressed as intensity ratios of the light emitted, reflected and fluoresced from the sample respectively, to the illumination light at each wavelength, with a suitable proportional constant. An object of the colorimetry is to obtain a measurement value analogous to visual observation. The color of a fluorescent sample is observed as an objective color, and accordingly is expressed by the total spectral radiance factor $B(\lambda)$, from which the colorimetric values are derived.

The CIE (International Committee of Illumination) defines spectral distributions (spectral intensities) of several standard illuminations such as Illuminants D65 and D50, (daylight), Illuminant A (incandescent lamp), and Illuminants F1 through F12 (fluorescent lamp), as illumination light to be used in colorimetry. For the evaluation of fluorescent samples, Illuminant D65 is generally used. The spectral excitation-fluorescence characteristics of a fluorescent sample is expressed by the Bi-spectral Luminescent Radiance Factor $F(\mu,\lambda)$, which is the matrix data showing the intensity of fluoresced light at wavelength $\lambda$ excited by monochromatic light at wavelength $\mu$ for illuminating the fluorescent sample surface with a unit intensity.

For instance, JP 2006-292510A (D1) discloses a practical method for obtaining the total spectral radiance factor $B(\lambda)$. D1 discloses a method comprising: calculating a total spectral radiance factor of a sample illuminated by test illumination, based on a bi-spectral fluorescent radiance factor or a bi-spectral radiance factor analogous to the sample, a spectral distribution of the test illumination, spectral distributions of first actual illumination light and second actual illumination light whose relative spectral distributions are different between an excitation wavelength region and a fluorescent wavelength region, and an actually measured spectral distribution of light emitted from the sample illuminated by the first actual illumination light and the second actual illumination light. The test illumination is illumination light to be used in evaluating an optical characteristic such as standard illuminant D65. The spectral distribution of emitted light is measured by e.g. a polychromator (spectral analyzer). More specifically, light emitted from a sample is dispersed by a diffraction grating provided in a polychromator at each wavelength, and the wavelength components of the light are incident into light receiving elements of a sensor array, respectively. An electric charge of each of the wavelength components incident into the respective corresponding light receiving elements is accumulated in accordance with the received light amount, and the accumulated electric charges are converted into electric signals for outputting. The sensor array is an image sensor such as a CCD (Charge-Coupled Device) sensor, an MOS (Metal Oxide Semiconductor) sensor, or a CMOS (Complementary Metal Oxide Semiconductor) sensor.

In an optical characteristic measuring apparatus using the method recited in D1, there is no need of using a fluorescent standard sample, and performing a cumbersome calibration using the fluorescent standard sample, thereby simplifying the measuring method or enhancing the measurement efficiency.

However, in the method recited in D1, optical characteristics of plural samples containing a fluorescent material cannot be accurately measured in a short time.

SUMMARY OF THE INVENTION

In view of the above, it is an object of the present invention to provide an optical characteristic measuring apparatus capable of accurately measuring optical characteristics of plural samples containing a fluorescent material in a short time by scanning the samples.

An optical characteristic measuring apparatus according to an aspect of the invention includes a sequentially-readable charge storage sensor array having a plurality of light receiving elements. First illumination light and second illumination light are controllably irradiated onto a sample containing a fluorescent material in such a manner that a period for irradiating the second illumination light onto the sample is included in an integration period of each of the light receiving elements for receiving a wavelength component of fluoresced light from the sample in measuring an optical characteristic of the sample. The optical characteristic measuring apparatus having the above arrangement enables to scan a plurality of samples containing a fluorescent material and accurately measure the optical characteristics of the samples in a short time.

These and other objects, features and advantages of the present invention will become more apparent upon reading the following detailed description along with the accompanying drawings.

BRIEF DESCRIPTION OF THE DRAWINGS

FIG. 8 is a timing chart in a first measuring method for measuring an optical characteristic of a sample by a scanning operation to be performed by an optical characteristic measuring apparatus.

FIGS. 9A and 9B are timing charts in a second measuring method for measuring an optical characteristic of a sample by a scanning operation to be performed by an optical characteristic measuring apparatus, wherein FIG. 9A is a timing chart in a first-time scanning operation, and FIG. 9B is a timing chart in a second-time scanning operation.

DETAILED DESCRIPTION OF THE PREFERRED EMBODIMENTS OF THE INVENTION

Figure 1:
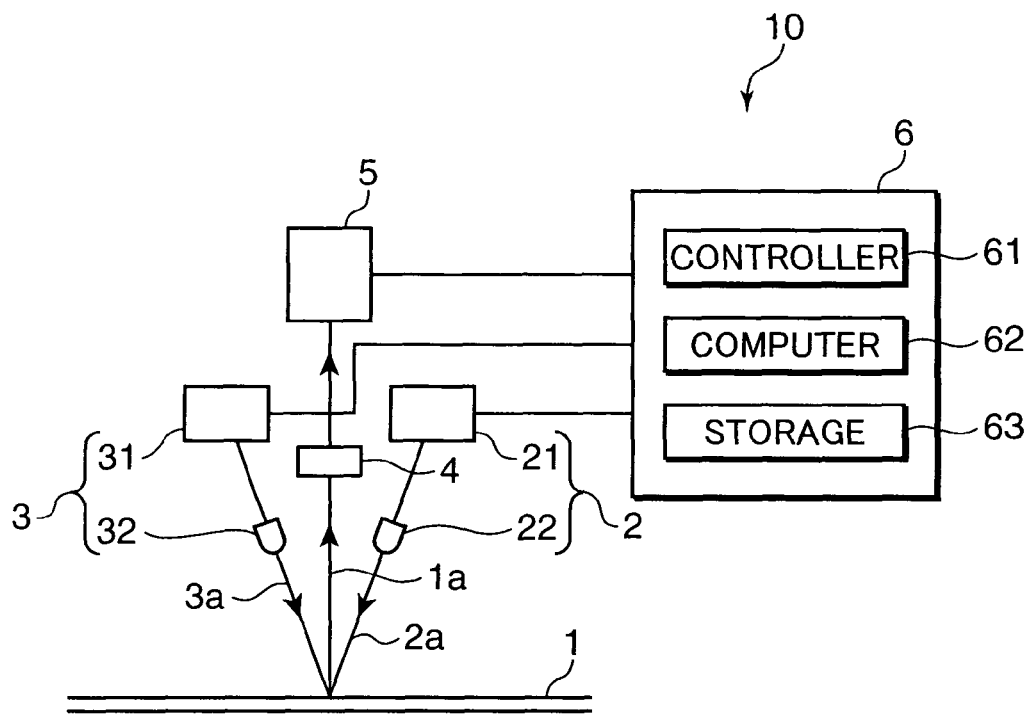
FIG. 1 is a schematic diagram showing an arrangement of an optical characteristic measuring apparatus embodying the invention.

In the following, an embodiment of the invention is described referring to the drawings. Elements having like reference numerals throughout the drawings have like arrangements, and repeated description thereof is omitted herein.

First, a technology to which the embodiment of the invention is applied is described. In the case where the colors to be printed by a color printer are calibrated, a series of color pieces for use in calibrating printing colors are scanned, and optical characteristics of the color pieces are measured. Similarly to the above, it is preferable to sequentially measure optical characteristics of a series of color pieces obtained by printing colors on FWA-treated paper, which may include the influence of fluoresced light, by scanning the color pieces by e.g. the method recited in D1. In the method recited in D1, it is necessary to measure light emitted from a sample by a polychromator incorporated in an optical characteristic measuring apparatus. In the polychromator loaded with a low-cost and sequentially-readable charge storage sensor array, the following drawback may be involved. The sequentially-readable system means a system for directly and sequentially reading out accumulated electric charges from light receiving elements, without using a transfer array for use in simultaneously transferring electric charges accumulated in an array of light receiving elements in parallel to each other. In other words, in the sequentially-readable system, an electric charge is accumulated in each of the light receiving elements during an integration period from a current readout operation to a succeeding readout operation with respect to a targeted light receiving element.

Figure 7:
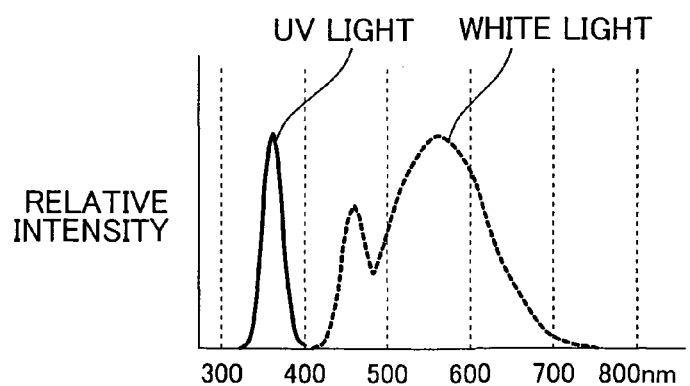
FIG. 7 is a graph showing relations between a wavelength and an intensity of UV light and white light.

The optical characteristic measuring apparatus recited in D1 has illuminators for irradiating UV light and white light, individually. The optical characteristic measuring apparatus is operable to acquire a spectral distribution of light to be emitted from a sample illuminated solely with white light, and a spectral distribution of light to be emitted from the sample illuminated with mixed light of white light and UV light by irradiation of the white light and the UV light, by controlling timings of the respective illuminations. FIG. 7 is a graph showing relations between a wavelength and an intensity of UV light and white light. In FIG. 7, the axis of abscissas indicates a wavelength in the unit of nm, and the axis of ordinate indicates a relative intensity. The spectral distributions of UV light and white light are expressed by e.g. the characteristics as shown in FIG. 7.

The sequentially-readable charge storage sensor array sequentially transmits readout pulses to the respective light receiving elements to read out electric charges accumulated in the respective light receiving elements. Upon receiving a readout pulse, a targeted light receiving element converts an integrated light amount of light, which has been incident into the light receiving element during an integration period from termination of a preceding readout cycle to start of a current readout cycle, into an electric signal, and outputs the electric signal. Accordingly, the integration periods of the respective light receiving elements are substantially identical to each other, and determined by a readout cycle. Phases of the cycles are different from each other depending on a readout timing. The readout cycle is a period during which readout pulses are transmitted to all the light receiving elements from a leading light receiving element to a trailing light receiving element. In the case where measurement is performed by scanning plural color pieces, a readout operation is repeated for about twenty times with respect to each of the color pieces during a scanning operation, several valid data are selected from the measurement data, and a measurement value is obtained by averaging the valid data.

In the method recited in D1, spectral distributions of light emitted from a sample are individually obtained by irradiating two illumination light whose relative spectral distributions are different from each other between an excitation wavelength region and a fluorescent wavelength region. Wavelength components of the spectral distributions of the two emitted light should be derived from two illumination light having substantially the same spectral distributions with each other. In the case where the optical characteristic measuring apparatus recited in D1 is loaded with the aforementioned sequentially-readable charge storage sensor array, and measurement is performed by scanning plural color pieces, it is necessary to adjust irradiation timings of two illumination light depending on integration periods of the respective light receiving elements so that an irradiation time of white light, or an irradiation time of mixed light becomes identical between the integration periods of the respective light receiving elements for receiving wavelength components of light emitted from the color pieces. In the following, switching timings between the illuminators are described.

FIG. 8 is a timing chart in a first measuring method for measuring an optical characteristic of a sample by a scanning operation to be performed by an optical characteristic measuring apparatus. The timing chart in the first measuring method shown in FIG. 8 is described. To simplify the description, light receiving elements $P_0$ through $P_n$, where n=7, are illustrated in FIG. 8. During a readout cycle Tr, readout pulses $p_0$ through $p_7$ are transmitted to the light receiving elements $P_0$ through $P_7$, respectively so that outputs from the light receiving elements $P_0$ through $P_7$ into which wavelength components $\lambda_0$ through $\lambda_7$ are respectively incident. Then, the outputs from the light receiving elements $P_0$ through $P_7$ are respectively read out during the pulse widths of the readout pulses $p_0$ through $p_7$. Further, the wavelength components $\lambda_0$ through $\lambda_7$ incident into the light receiving elements $P_0$ through $P_7$ during integration periods $T_0$ through $T_7$, each of which is a period from termination of a current readout pulse to start of a succeeding readout pulse, are accumulated in the light receiving elements $P_0$ through $P_7$ as electric charges, and the electric charges are outputted as electric signals. The output signals from the light receiving elements $P_0$ through $P_7$ are proportional to integrated light amounts of the wavelength components incident into the light receiving elements $P_0$ through $P_7$ during the integration period $T_0$ through $T_7$, respectively.

As shown in FIG. 8, a white LED (Light Emitting diode) is constantly driven, and a UV LED (Ultraviolet Light Emitting Diode) is driven during odd-numbered readout cycles Tr started with the readout pulse $p_0$, and driving of the UV LED is suspended during even-numbered readout cycles Tr started with the readout pulse $P_0$, and the driving operation and the suspending operation are alternately repeated. Thereby, mixed light and white light are alternately irradiated onto a sample at a cycle of two times of the readout cycle Tr. In the above arrangement, the mixed light is irradiated onto the light receiving element $P_0$ during all the odd-numbered integration periods $T_0$, and merely the white light is irradiated onto the light receiving element $P_0$ during all the even-numbered integration periods $T_0$. Thus, the mixed light and the white light are alternately irradiated onto the light receiving element $P_0$ during all the integration periods $T_0$. However, concerning the light receiving elements $P_1$ through $P_7$, the odd-numbered integration periods $T_1$ through $T_7$ respectively started with the readout pulses $p_1$ through $p_7$ do not coincide with the driving period of the UV LED. Specifically, the mixed light is irradiated during a part of the odd-numbered integration periods $T_1$ through $T_7$, and the white light is exclusively irradiated during the rest of the odd-numbered integration periods $T_1$ through $T_7$. Further, since the readout pulses $p_0$ through $p_7$ to be transmitted to the light receiving elements $P_0$ through $P_7$ are timewise displaced from each other, the ratios of mixed light irradiation periods with respect to the odd-numbered integration periods $T_1$ through $T_7$ are different from each other. Naturally, the ratios of mixed light irradiation periods with respect to the even-numbered integration periods $T_1$ through $T_7$ respectively started with the readout pulses $p_1$ through $p_7$ are different from each other, and the white light is exclusively irradiated during the rest of the even-numbered integration periods $T_1$ through $T_7$. As a result, spectral distributions of illumination light during the integration periods are different from each other at each wavelength component of emitted light. Thus, the method recited in D1 cannot be applied. Further, the ratio of mixed light irradiation period is substantially unchanged i.e. about 50%, regardless of whether or not an integration period is an odd-numbered integration period or an even-numbered integration period, concerning e.g. the integration period $T_3$ of the light receiving element $P_3$. Accordingly, the wavelength component $\lambda_3$ of emitted light, which is received on the light receiving element $P_3$ during an odd-numbered integration period and an even-numbered integration period, is not derived from two illumination light having relative spectral distributions different from each other. Accordingly, the total spectral radiance factor of an FWA-treated sample illuminated with test illumination cannot be accurately obtained by the method recited in D1.

Figure 9A:
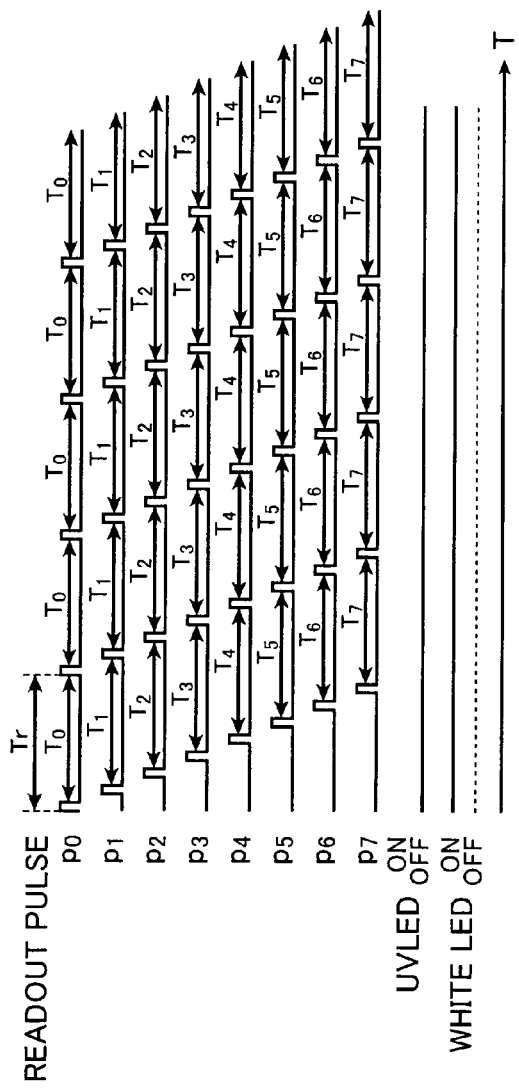
Figure 9B:
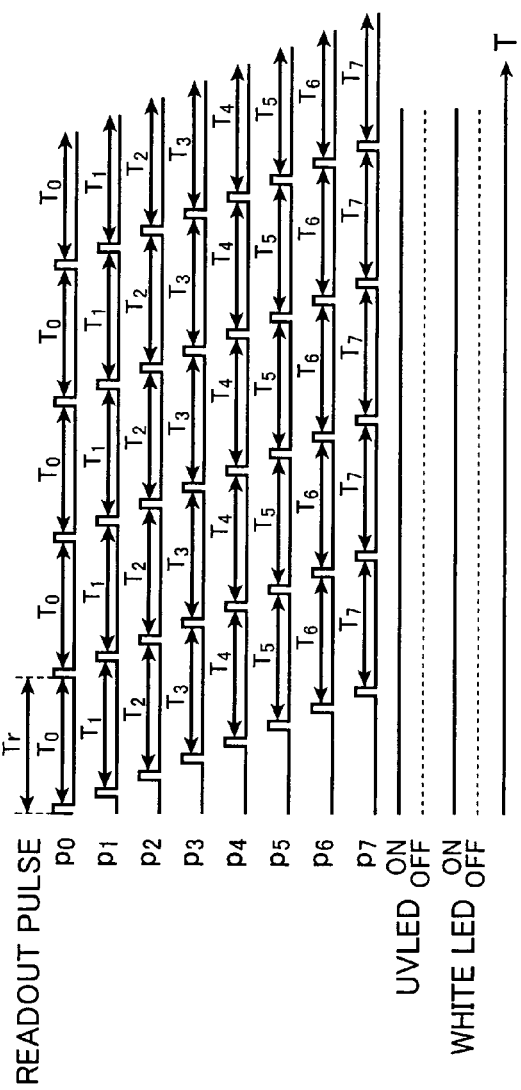

In view of the above, there is proposed a second measuring method, as a method for accurately obtaining the total spectral radiance factor of an FWA-treated sample by making spectral distributions of illumination light during integration periods of the wavelength components of emitted light constant. FIGS. 9A and 9B are timing charts in the second measuring method for measuring an optical characteristic of a sample by a scanning operation to be performed by an optical characteristic measuring apparatus. FIG. 9A is a timing chart in a first-time scanning operation, and FIG. 9B is a timing chart in a second-time scanning operation. In the following, timing charts of the second measuring method shown in FIGS. 9A and 9B are described.

First, in the first-time scanning operation shown in FIG. 9A, the UV LED is not driven, and solely the white LED is driven to irradiate white light onto a sample, and a spectral distribution of light emitted from the sample illuminated with the white light is measured. Then, in the second-time scanning operation shown in FIG. 9B, the UV LED and the white LED are simultaneously driven to irradiate mixed light of UV light and white light onto the sample, and a spectral distribution of light emitted from the sample illuminated with the mixed light is measured. Thereby, both of the illumination light i.e. the white light and the mixed light are irradiated during all the integration periods $T_0$ through $T_7$ of the light receiving elements $P_0$ through $P_7$. Thus, the spectral distributions of illumination light i.e. the white light and the mixed light during the integration periods of the wavelength components of light emitted from the sample illuminated with the white light and the mixed light can be made constant. This method, however, is cumbersome and an operation time is doubled, because it is necessary to perform a scanning operation two times by changing the illumination light.

Figure 10:
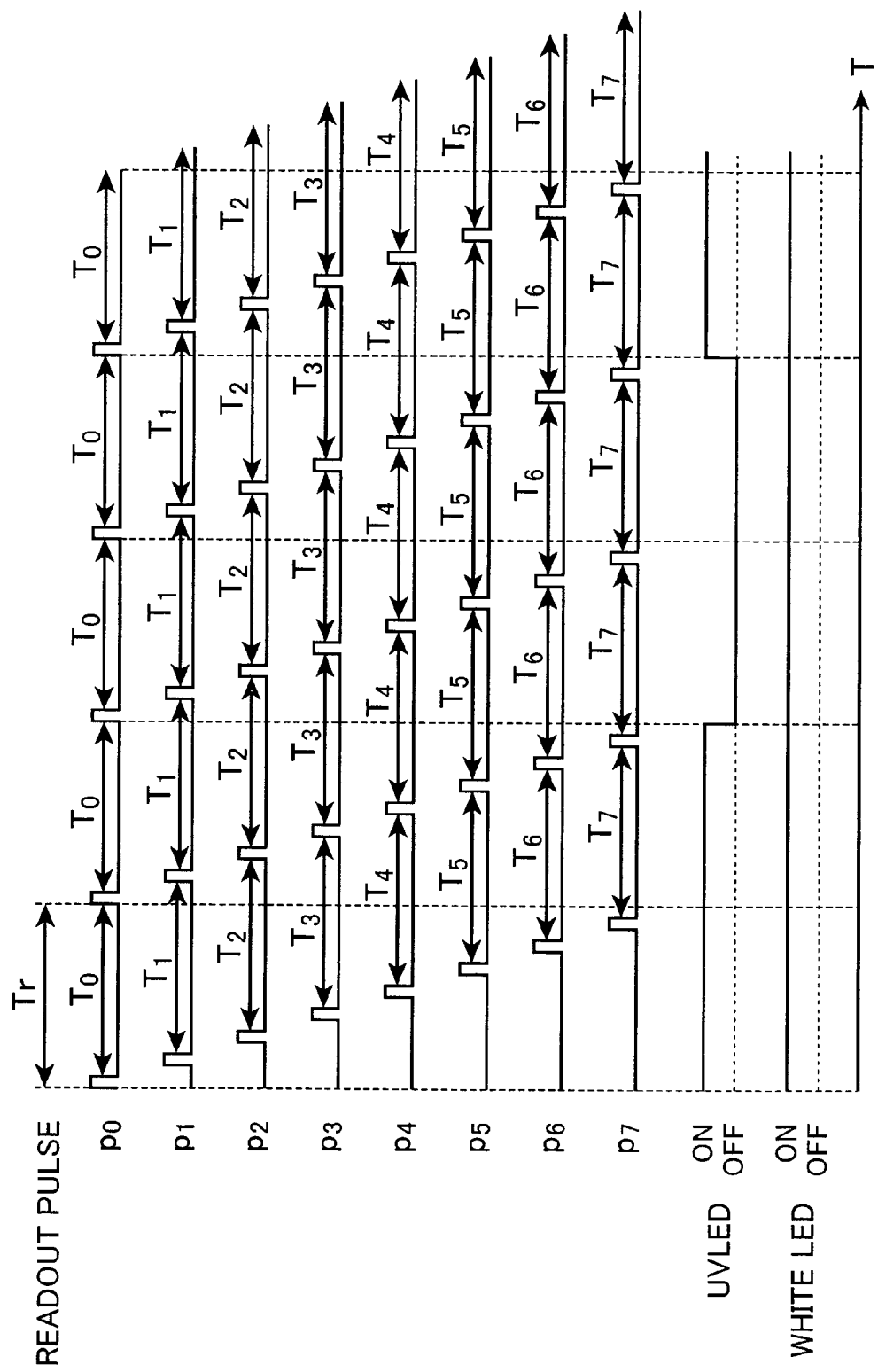
FIG. 10 is a timing chart in a third measuring method for measuring an optical characteristic of a sample by a scanning operation to be performed by an optical characteristic measuring apparatus.

There is proposed a third measuring method for accurately obtaining the total spectral radiance factor of a sample by: constantly driving a white LED, driving a UV LED for a period of two times of a readout cycle Tr, and suspending the driving of the UV LED for a period equal to the driving period of the UV LED, wherein the driving operation and the suspending operation of the UV LED are alternately repeated. In this method, a cycle of alternately irradiating white light and mixed light is four times of the readout cycle Tr. FIG. 10 is a timing chart in the third measuring method for measuring an optical characteristic of a sample by a scanning operation to be performed by an optical characteristic measuring apparatus. As shown in FIG. 10, the white LED is constantly driven, and a driving operation of the UV LED for a period of two times of the readout cycle Tr, and a suspending operation of driving of the UV LED for a period of two times of the readout cycle Tr are alternately repeated at a cycle of four times of the readout cycle Tr. Thereby, the mixed light or the white light is irradiated onto the light receiving element $P_0$ for a period corresponding to two cycles of the integration period $T_0$. Further, any one of the integration periods $T_1$ through $T_7$ (odd-numbered integration periods in FIG. 10) includes a period when the UV LED is driven or a period when driving of the UV LED is suspended, with respect to the light receiving elements $P_1$ through $P_7$, and the mixed light or the white light is irradiated onto the light receiving elements $P_1$ through $P_7$ during the odd-numbered integration periods $T_1$ through $T_7$. Accordingly, the spectral distributions of illumination light during the integration periods of wavelength components of emitted light are made constant during the odd-numbered integration periods $T_0$ through $T_7$ of the light receiving elements $P_0$ through $P_7$ in FIG. 10, and the method recited in D1 can be employed, using the spectral distributions of emitted light acquired during the odd-numbered integration periods $T_0$ through $T_7$.

In the third measuring method, however, there exist even-numbered integration periods $T_0$ through $T_7$ during which the mixed light and the white light are irradiated with a different ratio with respect to the light receiving elements $P_0$ through $P_7$, other than the odd-numbered integration periods $T_0$ through $T_7$ during which the mixed light or the white light is irradiated, during an operation period of the optical characteristic measuring apparatus. Measurement data obtained during the even-numbered integration periods $T_0$ through $T_7$ cannot be used in the method recited in D1. In other words, a half of the acquired data is useless data, and valid data is reduced to one half of the acquired data, which may lower the measurement precision. It is necessary to increase the number of readout operations so as to increase the number of valid data.

As described above, in the first measuring method, the spectral distributions of two illumination light cannot be made constant with respect to wavelength components of emitted light. In the second and the third measuring methods, the measurement time may be extended, and the measurement precision may be lowered.

In view of the above, in the embodiment, provided is an optical characteristic measuring apparatus capable of accurately measuring optical characteristics of samples containing a fluorescent material in a short time by scanning the samples. In the following, the optical characteristic measuring apparatus in this embodiment is described in detail.

FIG. 1 is a schematic diagram showing an arrangement of an optical characteristic measuring apparatus embodying the invention. As shown in FIG. 1, an optical characteristic measuring apparatus 10 includes a white illuminator (first illuminator) 2, a UV illuminator (second illuminator) 3, an objective lens 4, a polychromator (spectral analyzer) 5, and a computation controller (processor) 6 to measure an optical characteristic of a sample 1.

The sample 1 is a sample such as a fabric, paper, or a like product containing a fluorescent material, e.g. a printed sample for use in calibrating the colors to be printed by a color printer. Specifically, the sample 1 is constituted of a series of color pieces obtained by printing colors on FWA-treated paper containing a fluorescent whitening agent. It is preferable to sequentially measure optical characteristics of the color pieces i.e. the sample 1 by scanning the color pieces.

The white illuminator (first illuminator) 2 and the UV illuminator (second illuminator) 3 respectively irradiate white light 2a and UV light 3a. The white illuminator 2 has a white illumination driving circuit 21 and a white LED 22. The white LED 22 emits the white light 2a to illuminate the sample 1. The white illumination driving circuit 21 controls an operation of the white LED 22 i.e. controls the white LED 22 to drive and suspend the driving operation thereof. Alternatively, an incandescent lamp or a like device may be used in place of the white LED 22. The UV illuminator 3 has a UV illumination driving circuit 31 and a UV LED 32. Similarly to the white LED 22, the UV LED 32 emits the UV light 3a to illuminate the sample 1. The UV illumination driving circuit 31 controls an operation of the UV LED 32 i.e. controls the UV LED 32 to drive and suspend the driving operation thereof. Alternatively, a xenon flash lamp or a like device may be used as a light source for outputting a light flux in an UV wavelength region, in place of the UV LED 32. The white illumination driving circuit 21 and the UV illumination driving circuit 31 may be a circuit for driving a lamp to turn on and off based on pulse signals. An LED can be easily controlled, and has high stability and efficiency.

Figure 2:
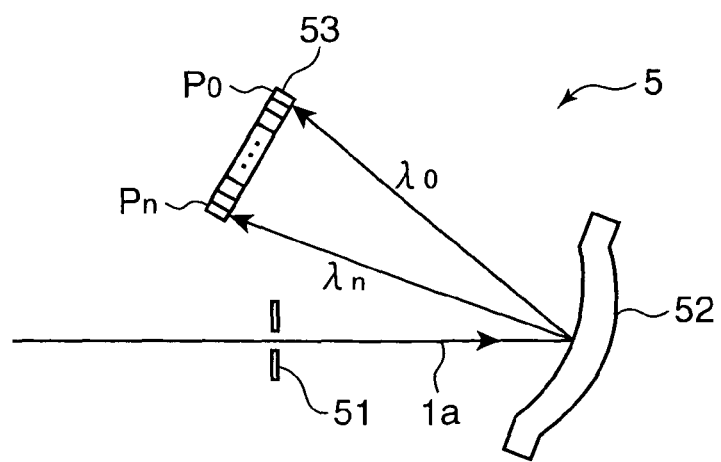
FIG. 2 is a diagram for describing an arrangement of a polychromator in the embodiment.

The computation controller 6 is constituted of an ROM (Read Only Memory) for storing various control programs, an RAM (Random Access Memory) for storing data to be used in a computing process or a controlling process, and a CPU (Central Processing Unit) for reading out the control programs from the ROM for execution. The computation controller 6 includes a controller 61, a computer 62, and a storage 63. The controller 61 controls the respective parts of the optical characteristic measuring apparatus 10 to perform a predetermined operation of the optical characteristic measuring apparatus 10. The computer 62 calculates an optical characteristic of a sample by applying a computing process such as calibration or weighted linear combination to data transmitted from the polychromator 5. The storage 63 stores therein an operation program of the optical characteristic measuring apparatus 10, data to be used in calibration, and data to be used in a weighting operation in performing the computing process The objective lens 4 condenses light emitted from the sample 1 illuminated with illumination light, and guides the condensed light to the polychromator 5. The polychromator 5 disperses the incident light into wavelength components, converts the light amount of each of the wavelength components into an electric signal, and outputs the electric signals. FIG. 2 is a diagram for describing an arrangement of the polychromator in the embodiment. As shown in FIG. 2, the polychromator 5 includes a slit 51 through which emitted light 1a is incident, a diffraction grating 52 for dispersing the incident emitted light 1a, and a charge storage sensor array 53 which includes light receiving elements $P_0$ through $P_n$ arranged in a direction aligned with the dispersing direction of the diffraction grating 52, and is adapted to output electric signals in accordance with light amounts of wavelength components $\lambda_0$ through $\lambda_1$, incident into the light receiving elements $P_0$ through $P_n$. The sensor array 53 is of sequentially-readable type. Electric charges accumulated in the light receiving elements $P_0$ through $P_n$ in accordance with the incident light amounts are directly and sequentially read out from the respective light receiving elements, without being transferred to a transfer array in parallel to each other. Since an integration period for accumulating an electric charge is from termination of a current readout pulse to start of a succeeding readout pulse, the phases of the integration periods are different from each other between the light receiving elements. The sensor array 53 includes one hundred and twenty-eight light receiving elements $P_n$ through $P_{127}$, for instance.

Although not shown in FIG. 1, preferably, the optical characteristic measuring apparatus 10 may include an output device such as a display device or a printer. The output device is operable to display or print e.g. a measurement value calculated by the computation controller 6. Since the optical characteristic measuring apparatus 10 is adapted to scan a series of samples, a driving device or a like device for performing a scanning operation may be provided. It is needless to say that a series of samples can be scanned by holding the optical characteristic measuring apparatus 10 by the operator and moving the optical characteristic measuring apparatus 10 relative to the series of samples, without using a driving device.

Figure 3:
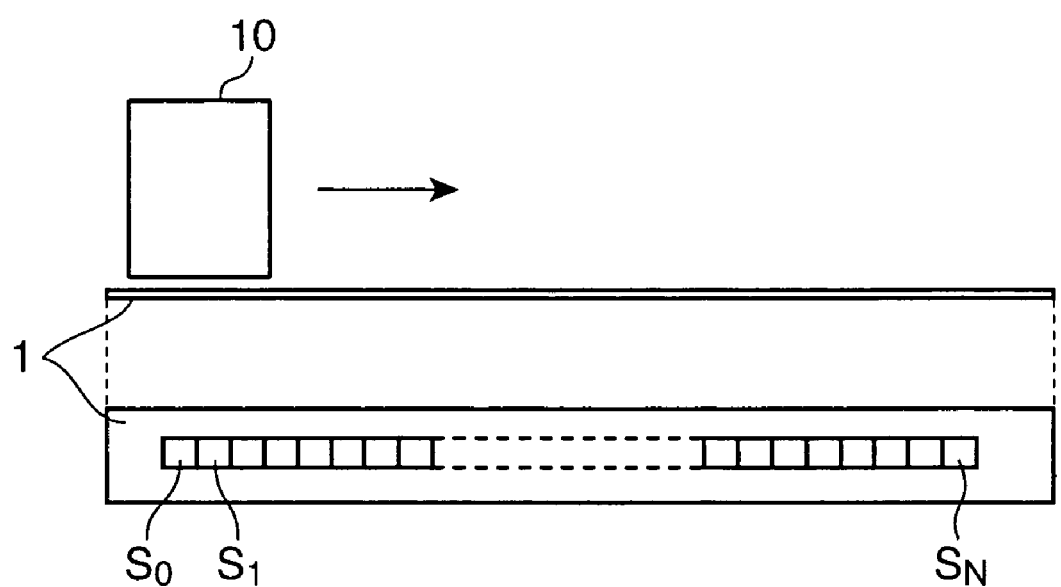
FIG. 3 is a diagram for describing how the optical characteristic measuring apparatus of the embodiment is operated.

Next, an operation to be performed by the optical characteristic measuring apparatus 10 of the embodiment is described. FIG. 3 is a diagram for describing how the optical characteristic measuring apparatus of the embodiment is operated. Referring to FIG. 3, the upper section is a side view of the sample 1 and the optical characteristic measuring apparatus 10, and the lower section is a plan view of the sample 1. As shown in the lower section in FIG. 3, the sample 1 is constituted of a series of color pieces $S_0$ through $S_N$ (where N is a positive integer) obtained by printing colors on FWA-treated paper. The optical characteristic measuring apparatus 10 measures optical characteristics of the color pieces $S_0$ through $S_N$ by scanning the color pieces $S_0$ through $S_N$ along an arranged direction (direction of the arrow in FIG. 3) of the color pieces $S_0$ through $S_N$. Similarly to the optical characteristic measuring apparatus used in the method recited in D1, the optical characteristic measuring apparatus 10 of the embodiment is an optical characteristic measuring apparatus which is provided with two illuminators for irradiating UV light and white light, respectively, and is adapted to calculate an optical characteristic of a sample, based on a spectral distribution of light emitted from the sample illuminated solely with white light, a spectral distribution of light emitted from the sample illuminated with mixed light of UV light and white light, and respective spectral distributions of white light and mixed light.

First, the operator places the optical characteristic measuring apparatus 10 above the sample 1, and moves the optical characteristic measuring apparatus 10 relative to the sample 1 to scan a series of color pieces. In response to start of a scanning operation, the controller 61 controls the white illumination driving circuit 21 and the UV illumination driving circuit 31 so that the white light 2a and the UV light 3a are irradiated onto the sample 1 at predetermined timings. In the case where solely the white light 1a is irradiated onto the sample 1, emitted light 1a from the sample 1 including reflected light from the sample 1 as a main component is incident into the polychromator 5 through the objective lens 4. In the case where mixed light of the white light 2a and the UV light 3a is irradiated onto the sample 1, emitted light 1a including reflected light from the sample 1, and fluoresced light excited by the UV light 3a as a main component, is incident into the polychromator 5 through the objective lens 4. The emitted light 1a including reflected light as a main component, and the emitted light 1a including reflected light and fluoresced light are spectrally measured with respect to each of the color pieces $S_0$ through $S_N$, and spectral distributions of these emitted light 1a are transmitted to the computation controller 6, as electric signals. Then, the computer 62 in the computation controller 6 calculates optical characteristics of the color pieces $S_0$ through $S_N$, using these spectral distribution data transmitted from the polychromator 5.

Figure 4:
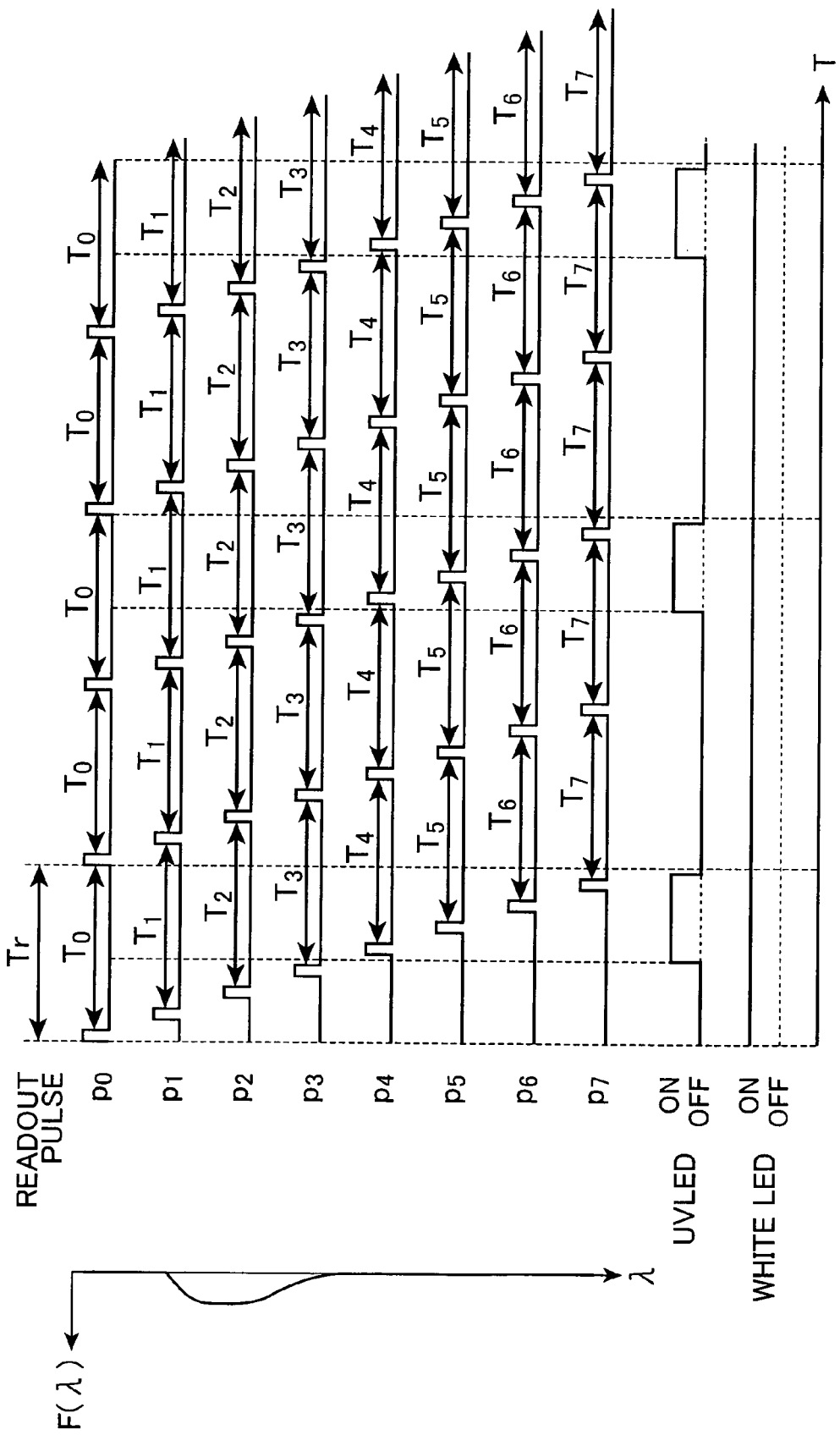
FIG. 4 is a timing chart in the case where an optical characteristic of a sample is measured by a scanning operation to be performed by the optical characteristic measuring apparatus of the embodiment.

Next, driving timings by the white LED 22 and the UV LED 32 are described. FIG. 4 is a timing chart, in the case where an optical characteristic of a sample is measured by the optical characteristic measuring apparatus of the embodiment by scanning the sample. The left section in FIG. 4 is a graph of a fluorescent spectral radiance factor $F(\lambda)$ to be read out from the light receiving elements $P_0$ through $P_7$ at each wavelength. To simplify the description, in FIG. 4, eight light receiving elements $P_0$ through $P_n$, where n=7, are illustrated. During a readout cycle Tr, readout pulses $p_0$ through $p_7$ are transmitted to the light receiving elements $P_0$ through $P_7$ into which wavelength components $\lambda_0$ through $\lambda_7$ are incident. Then, the outputs from the light receiving elements $P_0$ through $P_7$ are respectively read out during the pulse widths of the readout pulses $p_0$ through $p_7$. Further, the wavelength components $\lambda_0$ through $\lambda_7$ which are incident into the light receiving elements $P_0$ through $P_7$ during the integration periods $T_0$ through $T_7$, each of which is a period from termination of a current readout pulse to start of a succeeding readout pulse, are accumulated in the light receiving elements $P_0$ through $P_7$ as electric charges, and the electric charges are read out as electric signals corresponding to integrated light amounts of the wavelength components $\lambda_0$ through $\lambda_7$. In view of an aspect that measurement is performed by a scanning operation, integrations and readout operations are repeated plural times with respect to each of the color pieces. Since the charge storage sensor array 53 is of sequentially-readable type, as shown in FIG. 4, start timings of readout operations and integrations to be repeated with respect to the light receiving elements $P_0$ through $P_7$ are displaced from each other by Tr/8 in phase. The readout cycle Tr of the sensor array 53 constituted of one hundred and twenty-eight light receiving elements to be used in an actual operation is about several msec. Accordingly, readout operations can be performed about twenty times with respect to each of the color pieces. Several data out of the measurement data are selected as valid data, the valid data is subjected to a process such as an averaging process, and a measurement result by the averaging process is used as a measurement value on spectral distributions.

As shown in FIG. 4, the white LED 22 is constantly driven, and the UV LED 32 is driven at every other readout cycle Tr, more specifically, driven for one half of an integration period in a second half of each odd-numbered readout cycle Tr. Thereby, any of the integration periods $T_0$ through $T_3$ of the light receiving elements $P_0$ through $P_3$ includes the whole of the driving period (UV light irradiation period) of the UV LED 32 i.e. the second half of the odd-numbered readout cycle Tr. Driving of the UV LED 32 is suspended during the even-numbered readout cycles Tr. Thereby, the white light 2a is irradiated onto the sample 1 during all the odd-numbered integration periods $T_0$ through $T_3$ of the light receiving elements $P_0$ through $P_3$, and the UV light 3a is irradiated onto the sample 1 during one half of all the odd-numbered integration periods $T_0$ through $T_3$ of the light receiving elements $P_0$ through $P_3$. The above operation is substantially equivalent to an operation that mixed light of white illumination light, and UV illumination light having an intensity of one half of the intensity of the UV illumination light in a driving operation of the UV LED 32 is irradiated onto the sample 1 during all the odd-numbered integration periods $T_0$ through $T_3$ of the light receiving elements $P_0$ through $P_3$. Then, signals corresponding to the light emitted from the sample 1 irradiated with the mixed light are read out at the odd-numbered readout cycles of the light receiving elements $P_0$ through $P_3$. In the above arrangement, the ratio of the driving period of the UV LED 32 is set to one half of an integration period. Alternatively, the ratio of the driving period of the UV LED 32 may be set to a value other than one half. The modification is substantially equivalent to an operation that mixed light including UV illumination light having an intensity depending on the ratio is irradiated onto the sample 1 during all the odd-numbered integration periods. On the other hand, merely the white illumination light is irradiated onto the sample 1 during all the even-numbered integration periods $T_0$ through $T_3$ of the light receiving elements $P_0$ through $P_3$. Thus, light emitted from the sample 1 irradiated with mixed light and white light are alternately incident into the light receiving elements $P_0$ through $P_3$, with substantially the same spectral distributions during the integration periods $T_0$ through $T_3$ of the light receiving elements $P_0$ through $P_3$.

Concerning the light receiving elements $P_4$ through $P_7$, however, as shown in FIG. 4, the driving periods of the UV LED 32 are partially overlapped with the consecutive odd-numbered and even-numbered integration periods $T_4$ through $T_7$, and the ratio of the driving period of the UV LED 32 is different between the odd-numbered and even-numbered integration periods $T_4$ through $T_7$. Accordingly, emitted light to be incident into the light receiving elements $P_4$ through $P_7$ during the integration periods $T_4$ through $T_7$ of the light receiving elements $P_4$ through $P_7$ is different from the light which is emitted from the sample 1 irradiated with two illumination light, with substantially the same spectral distributions with respect to the light receiving elements $P_0$ through $P_3$.

Figure 5:
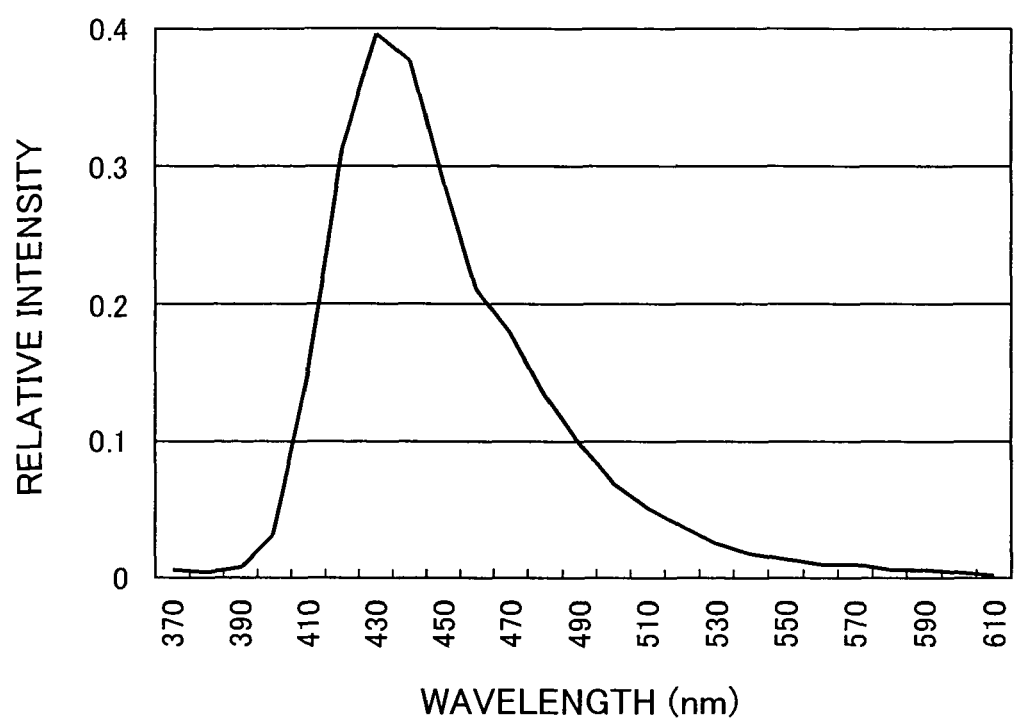
FIG. 5 is a graph showing relations between a wavelength and an intensity of fluoresced light.

In the following, a spectral characteristic of fluoresced light to be emitted from an FWA-treated sample is described. FIG. 5 is a graph showing relations between a wavelength and an intensity of fluoresced light. In FIG. 5, the axis of abscissas indicates a wavelength in the unit of nm, and the axis of ordinate indicates a relative intensity. As shown in FIG. 5, a relative spectral intensity distribution of fluoresced light to be emitted from a general FWA-treated sample has substantially no intensity at a wavelength of 590 nm or longer.

On the other hand, the method recited in D1 is a method for precisely obtaining a reflection characteristic of an FWA-treated sample, considering an influence of fluoresced light. Accordingly, in the method recited in D1, there is no need of using a wavelength region of 590 nm or longer, which is free from an influence of fluoresced light. Assuming that the light receiving wavelength region of the light receiving elements $P_4$ through $P_7$ is set to a wavelength region of 590 nm or longer, in other words, a wavelength region where fluoresced light substantially does not exist, even if UV light is irradiated onto the sample 1, and fluoresced light is excited and emitted from the sample 1, the fluoresced light is not incident into the light receiving elements $P_4$ through $P_7$. The relations between the fluoresced light and the light receiving elements $P_0$ through $P_7$ are indicated by the graph of the fluorescent spectral radiance factor $F(\lambda)$ shown in the left section in FIG. 4. In other words, the light receiving amount of a light receiving element having a light receiving wavelength region of 590 nm or longer is not changed, regardless of whether or not the light to be irradiated onto the sample 1 is white light or mixed light. Thus, an optical characteristic of the sample 1 in a wavelength region of 590 nm or longer can be obtained based on the spectral distributions of emitted light, without using the method recited in D1.

As described above, the emitted light 1a from the sample 1 irradiated with white light, or the emitted light 1a from the sample 1 irradiated with mixed light is incident, with substantially the same spectral distributions, into the light receiving elements $P_0$ through $P_3$, which has a light receiving wavelength region of 590 nm or shorter, where fluoresced light exists. An optical characteristic of the sample 1 in the wavelength region of 590 nm or shorter can be obtained based on the spectral distributions of the white light and the mixed light, using the method recited in D1. In other words, setting the light receiving wavelength region of the light receiving elements $P_4$ through $P_7$ to 590 nm or longer enables to obtain an optical characteristic of the sample 1 in the light receiving wavelength region of all the light receiving elements $P_0$ through $P_7$.

As described above, the optical characteristic measuring apparatus 10 of the embodiment is capable of accurately measuring optical characteristics of plural samples containing a fluorescent whitening agent by scanning the samples, using two illumination light whose spectral distributions are different from each other. The optical characteristic measuring apparatus 10 can obtain valid data of a sufficient amount by a one-time scanning operation, without performing a scanning operation plural times, and accurately measure optical characteristics of the samples. Accordingly, for instance, a series of color pieces obtained by printing colors on FWA-treated paper or a like substrate can be measured in a short time to calibrate the colors to be printed by a color printer.

The optical characteristic measuring apparatus 10 of the embodiment is described in detail. For instance, the sensor array 53 has one hundred and twenty-eight light receiving elements $P_0$ through $P_n$ (one hundred and twenty-eight pixels), and the wavelength range of the sensor array 53 is from about 340 nm to 840 nm. The wavelength range includes the wavelength region of the white light 2a and the wavelength region of the UV light 3a shown in FIG. 7. The first half of the light receiving elements i.e. the light receiving elements $P_0$ through $P_{63}$ receive wavelength components from about 340 nm to 590 nm, and the second half of the light receiving elements i.e. the light receiving elements $P_{64}$ through $P_{127}$ receive wavelength components from about 590 nm to 840 nm. The white LED 22 is constantly driven, and the UV LED 32 is driven in the second half of every other readout cycle Tr. In other words, the UV LED 32 is driven in such a manner that every other integration period of the integration periods $T_0$ through $T_{63}$ of the light receiving elements $P_0$ through $P_{63}$ includes a driving period of the UV LED 32. On the other hand, the UV LED 32 is partly driven during each of the integration periods $T_{64}$ through $T_{127}$ of the light receiving elements $P_{64}$ through $P_{127}$. In other words, any of the integration periods $T_{64}$ through $P_{127}$ does not include the whole of the driving period of the UV LED 32.

By performing the above operation, every other integration period of the integration periods $T_0$ through $T_{63}$ of the light receiving elements $P_0$ through $P_{63}$ equally includes the driving period of the UV LED 32. Accordingly, the output from the light receiving elements $P_0$ through $P_{63}$ is equivalent to a spectral distribution of light emitted from the sample 1 irradiated solely with the white light 2a, and a spectral distribution of the emitted light 1a from the sample 1 irradiated with mixed light of the white light 2a and the UV light 3a, wherein the spectral distributions are the same with respect to the light receiving elements $P_0$ through $P_{63}$, or information relating to the spectral distributions. On the other hand, the integration periods $T_{64}$ through $T_{127}$ of the light receiving elements $P_{64}$ through $P_{127}$ include the driving period of the UV LED 32 at a different ratio between each two consecutive integration periods of the integration periods $T_{64}$ through $T_{127}$. However, electric signals to be outputted from the light receiving elements $P_{64}$ through $P_{127}$ for receiving wavelength components in a wavelength region, where fluoresced light does not substantially have an intensity, are not affected by light from the UV LED 32. Accordingly, substantially the same spectral distributions of emitted light are obtained during all the integration periods $T_{64}$ through $T_{127}$. Thus, the optical characteristic measuring apparatus 10 of the embodiment is capable of accurately measuring an optical characteristic of the sample 1 by using the method of D1 in a wavelength region of 590 nm or shorter, and without using the method of D1 in a wavelength region of 590 nm or longer.

Figure 6:
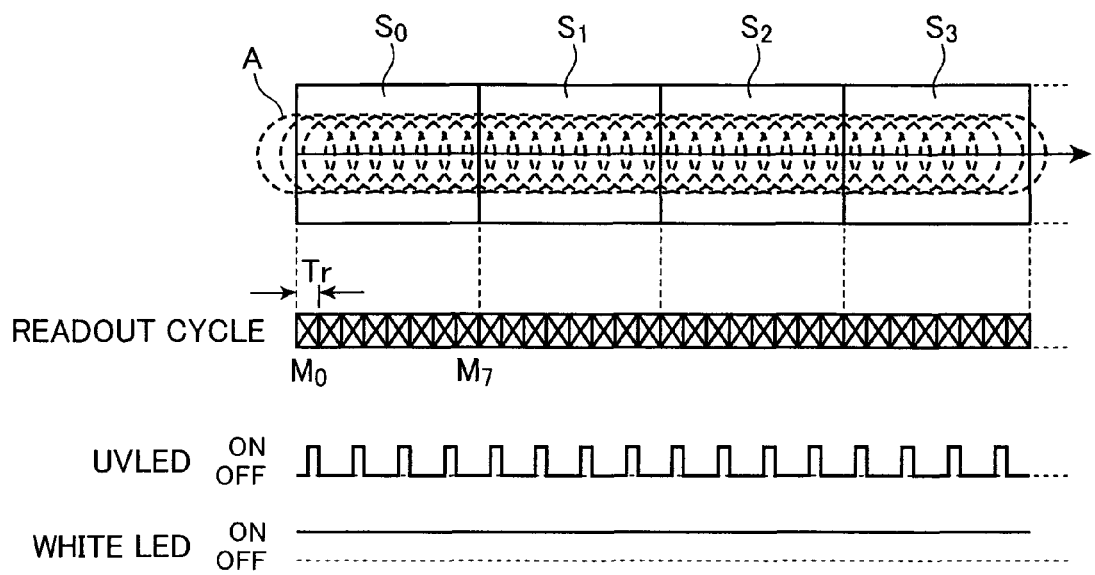
FIG. 6 is a diagram for describing readout timings with respect to each of color pieces to be performed by the optical characteristic measuring apparatus of the embodiment.

Readout timings of light receiving elements in the case where an optical characteristic of a sample constituted of a series of color pieces is measured by the optical characteristic measuring apparatus 10 of the embodiment is described referring to FIG. 6. FIG. 6 is a diagram for describing a readout timing with respect to each of the color pieces by the optical characteristic measuring apparatus of the embodiment. To simplify the description, the number of the light receiving elements is eight, and the number of color pieces is four. The optical characteristic measuring apparatus 10 of the embodiment performs a readout operation plural times while moving relative to each of the color pieces to measure plural measurement areas of each of the color pieces. FIG. 6 shows how the color pieces $S_0$ through $S_3$ are arranged, as well as plural measurement areas A of each of the color pieces $S_0$ through $S_3$, and readout timings of the measurement areas A. As described above, the optical characteristic measuring apparatus 10 constantly drives the white LED 22, and drives the UV LED 32 during a second half of each odd-numbered readout cycle Tr. Then, solely the white light $2a$, and mixed light of the white light $2a$ and the UV light $3a$ are alternately irradiated during the respective readout operations with respect to one measurement area A. For instance, in the case where the color piece $S_0$ is scanned, eight readout operations $M_0$ through $M_7$ are performed with respect to the light receiving elements $P_0$ through $P_7$ of the sensor array 53. After the targeted color piece is measured at the eight measurement areas A, measurement data obtained from several leading and trailing measurement areas of the eight measurement areas A, which may be affected by the adjacent color pieces, are deleted, and measurement data obtained from the several middle measurement areas of the targeted color piece are used as valid data. Then, out of the valid data, measurement data obtained from the odd-numbered measurement areas irradiated with the mixed light, and measurement data obtained from the even-numbered measurement areas irradiated with the white light are respectively subjected to an averaging process, and the average values are defined as measurement values by the respective illumination light i.e. the white light and the mixed light. In an actual operation, measurement is performed about twenty times with respect to each of the color pieces, several measurement data corresponding to several leading measurement areas and several trailing measurement areas are deleted to eliminate an influence from the adjacent color pieces, and the rest of the measurement data is used as valid data.

The measurement values obtained by the above operation are computed by the computer 62, using the method recited in e.g. D1 to obtain colorimetric values or like values. Specifically, a first spectral radiance factor of a sample illuminated by the first illumination light, and a second spectral radiance factor of the sample illuminated by the second illumination light are calculated, based on information measured by the spectral analyzer. The spectral radiance factors are subjected to linear combination using weights different from each other at each wavelength. Thereby, a spectral radiance factor of the sample illuminated by predetermined illumination light is obtained. Further, colorimetric values or like values are obtained by using the spectral radiance factor. Thus, the above arrangement eliminates the need of using a fluorescent standard sample and a cumbersome calibration using the fluorescent standard sample, thereby simplifying the measuring method or enhancing the measurement efficiency. Furthermore, accurate measurement of an optical characteristic of a sample by a scanning operation can be performed in a short time.

The specification discloses the technology having the above aspects. The following is a summary of the technology.

An optical characteristic measuring apparatus according to an aspect of the invention is an optical characteristic measuring apparatus for measuring an optical characteristic of a sample containing a fluorescent material. The apparatus includes: an illuminating section for irradiating first illumination light and second illumination light to illuminate the sample; a spectral analyzer for measuring spectral distributions of light emitted from the sample; and a processor for calculating the optical characteristic of the sample based on information obtained by successively irradiating the first illumination light and the second illumination light, and measuring the spectral distributions by the spectral analyzer, wherein the first illumination light and the second illumination light have spectral distributions different from each other in relative spectral distributions thereof between an excitation wavelength region and a fluorescent wavelength region of the fluorescent material, the spectral analyzer includes a sequentially-readable charge storage sensor array having a plurality of light receiving elements for respectively receiving wavelength components of the light emitted from the sample, the sequentially-readable charge storage sensor array being adapted to integrate the wavelength components received by the light receiving elements at phase different from each other, and perform a readout operation, the charge storage sensor array performs the integration and the readout operation plural times, and the processor measures the optical characteristic of the sample by controlling irradiation of the first illumination light and the second illumination light in such a manner that a period for irradiating the second illumination light onto the sample is included in an integration period of each of the light receiving elements for receiving a wavelength component of fluoresced light from the sample.

The above arrangement enables to realize an optical characteristic measuring apparatus capable of accurately measuring an optical characteristic of a sample containing a fluorescent material in a short time, using the first illumination light and the second illumination light. Specifically, the optical characteristic measuring apparatus enables to accurately measure optical characteristics of e.g. printed color samples containing a fluorescent whitening agent in a short time by scanning the printed color samples.

In the optical characteristic measuring apparatus, preferably, a cycle at which the second illumination light is irradiated in the integration period of each of the light receiving elements for receiving the wavelength component of the fluoresced light, and a cycle at which the irradiation of the second illumination light is suspended in the integration period may be alternately repeated during a cycle of the readout operation.

In the above arrangement, the spectral distributions of the emitted light illuminated by the first illumination light and the second illumination light are alternately and accurately measured. Accordingly, in the case where optical characteristics of a series of sample pieces are measured by a scanning operation by the optical characteristic measuring apparatus having the above arrangement, valid data free from an influence of adjacent sample pieces can be efficiently extracted with respect to each of the first illumination light and the second illumination light. Thereby, the optical characteristics of the sample pieces can be accurately measured.

In the optical characteristic measuring apparatus, preferably, the optical characteristic of the sample may be measured by scanning a series of sample pieces arranged in an array.

The above arrangement enables to measure optical characteristics of a series of color samples obtained by printing colors on FWA-treated paper for calibrating the colors to be printed by a color printer. Further, the optical characteristic measuring apparatus having the above arrangement enables to obtain valid data of a sufficient amount by a one-time scanning operation, without performing a scanning operation plural times, and accurately measure the optical characteristics of the color samples in a short time.

In the optical characteristic measuring apparatus, preferably, the first illumination light may be illumination light excluding ultraviolet light, and the second illumination light may be illumination light including the ultraviolet light.

In the above arrangement, since the first illumination light and the second illumination light have relative spectral intensities different from each other between an excitation wavelength region and a fluorescent wavelength region of the fluorescent material, the optical characteristic of the sample containing the fluorescent material can be accurately measured.

In the optical characteristic measuring apparatus, preferably, the illuminating section may include a second illuminator for irradiating the ultraviolet light, and a first illuminator for irradiating white light, the first illuminator may be exclusively driven to irradiate the first illumination light, and the first illuminator and the second illuminator may be simultaneously driven to irradiate the second illumination light.

In the above arrangement, the illumination light including the ultraviolet light, and the illumination light excluding the ultraviolet light can be easily irradiated.

In the optical characteristic measuring apparatus, preferably, the second illuminator may be a UV LED.

In the above arrangement, irradiation of the ultraviolet light can be easily controlled. Further, the UV LED has a long life, and high stability and efficiency.

In the optical characteristic measuring apparatus, preferably, the processor may derive a first spectral radiance factor of the sample illuminated by the first illumination light, and a second spectral radiance factor of the sample illuminated by the second illumination light, based on the information obtained by the measurement by the spectral analyzer, and derive a spectral radiance factor of the sample illuminated by predetermined illumination light by linearly combining the first spectral radiance factor and the second spectral radiance factor weighted by weights specific to each wavelength.

The above arrangement eliminates the need of using a fluorescent standard sample and a cumbersome calibration using the fluorescent standard sample, thereby simplifying the measuring method or enhancing the measurement efficiency. More specifically, the method recited in D1 can be used.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. An optical characteristic measuring apparatus for measuring an optical characteristic of a sample containing a fluorescent material, the apparatus comprising:
    an illuminating section for irradiating first illumination light and second illumination light to illuminate the sample;
    a spectral analyzer for measuring spectral distributions of light emitted from the sample; and
    a processor for calculating the optical characteristic of the sample based on information obtained by successively irradiating the first illumination light and the second illumination light, and measuring the spectral distributions by the spectral analyzer, wherein
    the first illumination light and the second illumination light have spectral distributions different from each other in relative spectral distributions thereof between an excitation wavelength region and a fluorescent wavelength region of the fluorescent material,
    the spectral analyzer includes a sequentially-readable charge storage sensor array having a plurality of light receiving elements for respectively receiving wavelength components of the light emitted from the sample, the sequentially-readable charge storage sensor array being adapted to integrate the wavelength components received by the light receiving elements at phase different from each other, and perform a readout operation,
    the charge storage sensor array performs the integration and the readout operation plural times, and
    the processor measures the optical characteristic of the sample by controlling irradiation of the first illumination light and the second illumination light in such a manner that a period for irradiating the second illumination light onto the sample is included in an integration period of each of the light receiving elements for receiving a wavelength component of fluoresced light from the sample.

2. The optical characteristic measuring apparatus according to claim 1, wherein
    a cycle at which the second illumination light is irradiated in the integration period of each of the light receiving elements for receiving the wavelength component of the fluoresced light, and a cycle at which the irradiation of the second illumination light is suspended in the integration period are alternately repeated during a cycle of the readout operation.

3. The optical characteristic measuring apparatus according to claim 2, wherein
    the optical characteristic of the sample is measured by scanning a series of sample pieces arranged in an array.

4. The optical characteristic measuring apparatus according to claim 1, wherein
    the first illumination light is illumination light excluding ultraviolet light, and
    the second illumination light is illumination light including the ultraviolet light.

5. The optical characteristic measuring apparatus according to claim 4, wherein
    the illuminating section includes a second illuminator for irradiating the ultraviolet light, and a first illuminator for irradiating white light,
    the first illuminator is exclusively driven to irradiate the first illumination light, and
    the first illuminator and the second illuminator are simultaneously driven to irradiate the second illumination light.

6. The optical characteristic measuring apparatus according to claim 5, wherein
    the second illuminator is a UV LED.

7. The optical characteristic measuring apparatus according to claim 1, wherein
    the processor derives a first spectral radiance factor of the sample illuminated by the first illumination light, and a second spectral radiance factor of the sample illuminated by the second illumination light, based on the information obtained by the measurement by the spectral analyzer, and derives a spectral radiance factor of the sample illuminated by predetermined illumination light by linearly combining the first spectral radiance factor and the second spectral radiance factor weighted by weights specific to each wavelength.

* * * * *